United States Patent
Morita et al.

(10) Patent No.: US 6,238,656 B1
(45) Date of Patent: *May 29, 2001

(54) COSMETIC RAW MATERIALS, COSMETIC PRODUCTS, AND METHODS OF MANUFACTURING COSMETIC PRODUCTS

(75) Inventors: Yoshitsugu Morita; Kazuo Kobayashi; Ryuji Tachibana; Tadashi Hamachi; Masaru Ozaki, all of Chiba Prefecture (JP)

(73) Assignee: Dow Corning Toray Silicone Corporation, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/335,028

(22) Filed: Jun. 17, 1999

(30) Foreign Application Priority Data

Jun. 23, 1998 (JP) .................................................. 10-192507
Jan. 25, 1999 (JP) .................................................. 11-016277

(51) Int. Cl.$^7$ ........................................................ A61K 7/06
(52) U.S. Cl. .................................. 424/70.12; 424/70.122; 514/938
(58) Field of Search .............................. 424/401, 70.12, 424/70.122; 514/938

(56) References Cited

U.S. PATENT DOCUMENTS

| | | | |
|---|---|---|---|
| 4,980,167 | 12/1990 | Harashima et al. | 424/401 |
| 5,154,849 | 10/1992 | Visscher et al. | 252/174 |
| 5,854,336 | * 12/1998 | Divone, Sr. et al. | |
| 5,928,660 | * 7/1999 | Kobayashi et al. | |
| 6,057,386 | * 5/2000 | Morita et al. | |
| 6,060,546 | * 5/2000 | Powell et al. | |

OTHER PUBLICATIONS

Abstract of Japanese Patent 07330537; Jun. 02, 1994.
Abstract of Japanese Patent 02172906, Dec. 26, 1988.
Abstract of Japanese Patent 05139932, Nov. 12, 1991.
Abstract of Japanese Patent 10036228, Jul. 18, 1996.
Abstract of Japanese Patent, 05262987, Mar. 18, 1992.

* cited by examiner

*Primary Examiner*—Diana Dudash
*Assistant Examiner*—Alysia Berman
(74) *Attorney, Agent, or Firm*—James L. DeCesare

(57) ABSTRACT

A cosmetic raw material provides uniform dispersions of silicone oils and crosslinked silicone particles in cosmetic products. The cosmetic products consist of the cosmetic raw material combined with other types of cosmetic raw materials. This provides pleasant sensations of touch with the fingers and skin, improved rubbing properties, and sensation in their use. The method of manufacturing the cosmetic products has a high efficiency. The cosmetic raw material is made from a silicone oil emulsion containing crosslinked silicone particles having an average diameter of 0.05–100 $\mu$m which are contained in silicone oil drops having an average diameter of 0.1–500 $\mu$m, the drops in turn being dispersed in water. The diameter of the crosslinked silicone particles is less than the diameter of the silicone oil drops.

3 Claims, No Drawings

COSMETIC RAW MATERIALS, COSMETIC PRODUCTS, AND METHODS OF MANUFACTURING COSMETIC PRODUCTS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present invention relates to a cosmetic raw material, a cosmetic product, and to a method for manufacturing a cosmetic product. More specifically, the invention concerns a cosmetic raw material which is a silicone oil and crosslinked silicone particles that can be uniformly dispersed in a cosmetic product; a cosmetic product which is prepared from the cosmetic raw material in combination with another cosmetic raw material, which has a good feeling on fingers and skin, good spreading characteristics, and good feeling during use, and which prevents hair from "flying away" and tangling, have good hair set retention, and add dryness and freedom from oiliness to hair; and a method of manufacturing the cosmetic product.

BACKGROUND OF THE INVENTION

It is known to improve the smoothness and touch sensation of a cosmetic product by utilizing a silicone oil, crosslinked silicone particles, or combinations of both as a cosmetic raw material from which a cosmetic product is prepared. Cosmetic products prepared by utilizing both a silicone oil and crosslinked silicone particles are known.

For example, Japanese Laid Open Patent Applications [Kokai] Hei 1-165,509 and Hei 1-190,757, describe cosmetic products formed by compounding crosslinked silicone particles having three dimensional net like structures, with a silicone oil of high or low viscosity.

Japanese Laid Open Patent Application [Kokai] Hei 1-207,354 describes a cosmetic product composed of a crosslinked silicone of a hydrosilation crosslinkable silicone composition and a silicone oil of low viscosity.

Japanese Laid Open Patent Application [Kokai] Hei 3-79,669 describes a cosmetic product prepared from a crosslinked silicone, a low viscosity silicone oil, a polyoxyalkylene modified silicone type surface active agent, and water.

Japanese Laid Open Patent Application [Kokai] Hei 3-271,211 describes a cosmetic foundation that comprises a silicone oil emulsion composed of a low viscosity silicone oil and a silicone which is a solid at room temperature.

Japanese Laid Open Patent Application [Kokai] Hei 6-502,646 (U.S. Pat. No. 5,154,849 issued Oct. 13, 1992), describes a skin cleansing composition composed of a silicone rubber and a silicone oil.

Japanese Laid Open Patent Application [Kokai] Hei 7-330,537 describes a cosmetic product composed of a high molecular weight silicone and a silicone rubber.

Japanese Laid Open Patent Application [Kokai] Hei 2-172,906, Hei 5-139,932, and Hei 10-36228 describe hair cosmetic products composed of a silicone oil and a crosslinked silicone particle. More specifically, Japanese Laid Open Patent Application [Kokai] Hei 2-243612 (U.S. Pat. No. 4,980,167 issued Dec. 25, 1990), and Hei 5-262987 describe hair cosmetic products comprised of a crosslinked silicone particle with a silicone oil.

However, since these cosmetic products are prepared from cosmetic raw materials comprising a silicone oil and crosslinked silicone particles compounded with another cosmetic raw material, their manufacture is a problem. In particular, the crosslinked silicone escannot be sufficiently dispersed in the cosmetic product; the silicone oil and the crosslinked silicone particles have poor affinity to each other; and when mixed together, they lose their original properties.

More specifically, when water based cosmetic products are prepared and a silicone oil and crosslinked silicone particles are dispersed in another cosmetic raw material, it becomes impossible to develop a sufficient shear force, such that the resulting cosmetic product either cannot acquire sufficient stability or it produces unpleasant sensations in its application.

BRIEF SUMMARY OF THE INVENTION

It is an object of the present invention to provide a cosmetic raw material that allows uniform dispersion of a silicone oil and crosslinked silicone particles in a cosmetic product; a cosmetic product prepared from the cosmetic raw material in combination with another cosmetic raw material, which is pleasant to the touch by the fingers and skin, which has good spreadability and a pleasant feeling when applied, which prevent hair from "flying away" and tangling, have good hair set retention, and add dryness and freedom from oiliness to hair; and to a method of manufacturing the cosmetic product.

The cosmetic raw material of the present invention is a silicone oil emulsion which contains crosslinked silicone particles having an average diameter of 0.05 to 100 $\mu$m, in silicone oil drops having an average diameter of 0.1 to 500 $\mu$m, dispersed in water. The diameter of the crosslinked silicone particles are smaller than the diameter of the silicone oil drops.

In another embodiment, the cosmetic raw material is characterized by being a silicone composition obtained by removing water from the above silicone oil emulsion, and which contains the crosslinked silicone particles dispersed in the silicone oil.

In a further embodiment, a cosmetic product is provided which is a cosmetic raw material prepared from the above silicone oil emulsion in combination with another cosmetic raw material.

In yet another embodiment, the cosmetic product is a cosmetic raw material prepared from the above silicone composition in combination with another cosmetic raw material.

In the final embodiment, there is provided a method of manufacturing a cosmetic product by compounding the cosmetic raw material prepared from the above silicone oil emulsion in combination with another cosmetic raw material.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

As noted above, the cosmetic raw material in one embodiment of the present invention is characterized by being a silicone oil emulsion having crosslinked silicone particles in silicone oil drops dispersed in water.

The crosslinked silicone particles contained in the emulsion can be produced by subjecting a crosslinkable silicone composition to a hydrosilation crosslinking reaction, a condensation crosslinking reaction, crosslinking with the use of an organic peroxide, or crosslinking caused by irradiation with high energy rays. Most preferable are hydrosilation and condensation crosslinking reactions.

There are no special limitations with regard to the type of the oil used in the emulsion for forming the silicone oil drops. Preferably, however, is should be a silicone oil having a linear, partially branched linear, cyclic, or branched molecular structure. Most preferably, the silicone oils should have a linear or a cyclic structure. It is preferred that the silicone oil not participate in the crosslinking reaction during the formation of the crosslinked silicone particles. In other words, when the crosslinked silicone particles are formed by a hydrosilation crosslinking reaction, it should be a silicone oil which does not contain in its molecules alkenyl groups or silicon bonded hydrogen atoms.

Thus, the silicone oil can be a dimethylpolysiloxane having both molecular terminals capped with trimethylsiloxy groups, a methylphenylpolysiloxane having both molecular terminals capped with trimethylsiloxy groups, a copolymer of methylphenylsiloxane and dimethylsiloxane having both molecular terminals capped with trimethylsiloxy groups, a copolymer of methyl-(3,3,3-trifluoropropyl)siloxane and dimethylsiloxane having both molecular terminals capped with trimethylsiloxy groups, a cyclic dimethylsiloxane, or a cyclic methylphenylsiloxane.

When the crosslinked silicone particles are formed by means of a condensation crosslinking reaction, the oil should not contain in its molecule any silanol groups, silicon bonded hydrogen atoms, or silicon bonded hydrolyzable groups. For example, the silicone oil could be similar to any of the oils mentioned above, or a dimethylpolysiloxane having both molecular terminals capped with dimethylvinylsiloxy groups, a copolymer of methylvinylsiloxane and dimethylsiloxane having both molecular terminals capped with dimethylvinylsiloxy groups, a methylvinylpolysiloxane having both molecular terminals capped with trimethylsiloxy groups, or a cyclic methylvinylsiloxane. The silicone oil should have a viscosity of 1 to 100,000,000 mPa.s, preferably 2 to 10,000,000 mPa.s measured at 25° C.

The average diameter of the silicone oil drops in the emulsion of the present invention should be within a range of 0.1 to 500 μm, preferably 0.2 to 500 μm, more preferably 0.5 to 500 μm, most preferably 0.5 to 200 μm. This is because a cosmetic raw material in the form of an emulsion with an average diameter of silicone oil drops below the lower range or above the upper limit of the range will have low stability.

The average diameter of the crosslinked silicone particles in the emulsion of the present invention should be within a range of 0.05 to 100 μm, preferably 0.1 to 100 μm, more preferably 0.1 to 50 μm. This is because, with an average diameter of particles in the emulsion exceeding the upper limit, it would be difficult to uniformly mix the cosmetic raw material of the invention with another cosmetic raw material, whereby the obtained cosmetic product will have insufficient feeling on the fingers and skin, and poor stability.

The emulsion of the present invention may be produced in the form of a liquid, a cream, or a paste. In the emulsion, the diameter of the crosslinked silicone particles should be smaller than the diameter of the silicone oil drops. The crosslinked silicone particles may have a spherical, thread like, flat, or irregular shape. The spherical shape is preferable.

The emulsion can be prepared by dispersing a crosslinkable silicone composition containing a non-crosslinkable silicone oil in water, and causing a crosslinking reaction. The non-crosslinkable silicone oil should be used in an amount that exceeds the amount of non-crosslinkable silicone oil that can be held by the crosslinked product which is obtained from the crosslinkable silicone composition.

The crosslinkable silicone composition suitable for use in methods of the invention include compositions which can crosslink by means of hydrosilation reactions, condensation reactions, organic peroxide induced reactions, or which crosslink by irradiation with high energy rays. Crosslinking obtained by hydrosilation reactions and condensation reactions is preferred.

Hydrosilation type crosslinkable silicone compositions include organopolysiloxanes having in their molecule at least two alkenyl groups, organopolysiloxanes having in the molecule at least two silicon bonded hydrogen atoms, and a catalyst for the hydrosilation reaction. In accordance with the method of the invention, the crosslinkable silicone composition is first combined with the hydrosilation reaction catalyst in water. This is accomplished by dispersing in water the crosslinkable silicone composition premixed with a hydrosilation reaction catalyst, or by first dispersing the crosslinkable silicone composition in water, and then adding the hydrosilation reaction catalyst to water. It is preferred to use an aqueous dispersion having dispersed particles of the hydrosilation reaction catalyst with an average diameter of less than 1 μm.

Condensation type crosslinkable silicone compositions include organopolysiloxanes which contain at least two hydrolyzable groups such as aminoxy groups, acetoxy groups, oxime groups, alkoxy groups, or hydroxyl groups, bonded to silicon atoms in its molecule; a silane type crosslinking agent having at least three hydrolyzable groups such as aminoxy groups, acetoxy groups, oxime groups, alkoxy groups, bonded to silicon atoms in its molecule; and a condensation reaction catalyst, such as an organic titanium compound or an organic tin compound.

A filler can be added to the crosslinkable silicone composition for adjusting its flowability, or for improving the mechanical strength of the resulting crosslinked silicone particles. Some examples of fillers are precipitated silica, fumed silica, baked silica, fumed titanium oxide, or other types of similar reinforcing fillers; crushed quartz, diatomaceous earth, aluminum silicate, ferrous oxide, zinc oxide, calcium oxide, or other types of similar non-reinforcing fillers. The surfaces of these fillers can be treated with hexamethyldisilazane, trimethylchlorosilane, polydimethylsiloxane, polymethylhydrogensiloxane, or other types of similar organosilicon compounds. It is preferred that the crosslinkable silicone composition be one which, as a result of crosslinking, produces a rubber like, gel like, or elastomer like crosslinked substance.

The non-crosslinkable silicone oil contained in the crosslinkable silicone composition should be one that does not participate in the crosslinking of the composition. It may have a linear, partially branched linear, cyclic, or branched molecular structure. Linear and cyclic structures are preferred, however.

For compositions which crosslink by a hydrosilation reaction, the non-crosslinkable silicone oil should not contain alkenyl groups or silicon bonded hydrogen atoms in its molecule. Examples of suitable oils are dimethylpolysiloxanes having both molecular terminals capped with trimethylsiloxy groups, methylphenylpolysiloxanes having both molecular terminals capped with trimethylsiloxy groups, copolymers of methylphenylsiloxane and dimethylsiloxane having trimethylsiloxy groups on both molecular terminals, copolymers of methyl (3,3,3-trifluoropropyl) siloxane and dimethylsiloxane having trimethylsiloxy groups on both molecular terminals, cyclic dimethylsiloxanes, cyclic methylphenylsiloxanes, and glycidoxypropyl modified polyorganosiloxanes.

For compositions which crosslink by a condensation reaction, the oil should be free of silanol groups, silicon bonded hydrogen atoms, and silicon bonded hydrolyzable groups. This includes the silicone oils listed above, as well as dimethylpolysiloxanes having both of molecular terminals capped with dimethylvinylsiloxy groups, copolymers of methylvinylsiloxane and dimethylsiloxane having dimethylvinylsiloxy groups on both molecular terminals, methylvinylpolysiloxanes having trimethylsiloxy groups at both molecular terminals, cyclic methylvinylsiloxanes, polyethylene or polypropylene oxide modified polyorganosiloxanes, and hexyl or dodecyl containing alkyl modified polyorganosiloxanes. The non-crosslinkable silicone oils should have at 25° C. a viscosity within the range of 1 to 100,000,000 mPa.s, preferably 2 to 10,000,000 mPa.s.

The non-crosslinkable silicone oil contained in the crosslinkable silicone composition should be used in an amount sufficient to maintain it in the product of crosslinking of the crosslinkable silicone composition. More specifically, it should be used in excess of the quantity of noncrosslinkable oil that can be held by the product of crosslinking. The amount will vary depending upon the use of different combinations of crosslinkable silicone compositions and non-crosslinkable silicone oils. In general, however, the non-crosslinkable silicone oil should be used in an amount within a range of 200 to 5,000 parts by weight, preferably 250 to 2,000 parts by weight, based upon 100 parts by weight of crosslinkable silicone composition.

The method for preparing emulsions according to the invention may include dispersing the crosslinkable silicone composition containing the non-crosslinkable silicone oil in water, and then conducting the crosslinking reaction. The dispersing step of the method can be carried out using a homomixer, paddle mixer, Henschel mixer, homodisperser, colloid mixer, propeller type stirrer, homogenizer, in line type continuous emulsifier, ultrasonic emulsifier, or vacuum kneader.

While there are no special limitations on the amount of water that can be used, preferably it should be used in an amount of 5 to 99 percent by weight, more preferably 10 to 80 percent by weight, based on the total weight of the emulsion.

To improve the stability of the crosslinkable silicone composition in water and to ensure its dispersion, it can be combined with a nonionic surface active agent, a cationic surface active agent, or an anionic surface active agent. The most preferred surface active agent is the nonionic type. The surface active agent should be used in an amount of 0.1 to 20 parts by weight, preferably 0.5 to 10 parts by weight, based on 100 parts by weight of the crosslinkable silicone composition containing the noncrosslinkable silicone oil.

Emulsions of crosslinkable silicone composition are then heated, maintained at room temperature, or irradiated with high energy rays, whereby crosslinking occurs in a water dispersion of the crosslinkable silicone composition.

Some examples of optional ingredients that can be used in cosmetic raw materials according to this invention are organic oils such as liquid paraffin, isoparaffin, hexyl laurate, isopropyl myristate, myristil myristate, cetyl myristate, 2-octyldodecyl myristate, isopropyl palmitate, 2-ethylhexyl palmitate, butyl stearate, decyl oleate, 2-octyldodecyl oleate, myristil lactate, cetyl lactate, lanolin acetate, stearic alcohol, cetostearic alcohol, oleic alcohol, avocado oil, almond oil, olive oil, cacao oil, jojoba oil, sesame oil, safflower oil, soybean oil, camellia oil, squalane, persic oil, castor oil, mink oil, cotton seed oil, coconut oil, egg yolk oil, beef tallow, lard, polypropylene glycol monooleate, neopentylglycol 2-ethylhexanoate, or similar glycol ester oil; triglyceryl isostearate, triglyceryl cocoate, or similar polyhydric alcohol ester oil; polyoxyethylene lauryl ether, polyoxypropylene cetyl ether, or similar polyoxyalkylene ether.

While the silicone oil emulsion can be prepared by uniformly dispersing crosslinked silicone particles in a silicone oil and then emulsifying the dispersion, the crosslinked silicone particles and the silicone oil drops may disperse separately, and therefore it may be difficult to prepare silicone oil emulsions containing crosslinked silicone particles in silicone oil drops dispersed in water. Thus, even though such silicone oil emulsions can be used as cosmetic raw materials, in some final cosmetic products, the silicone oil and the crosslinked silicone particles may be nonuniformly dispersed.

Another embodiment of a cosmetic raw material of the invention is a silicone composition having crosslinked silicone particles dispersed in silicone oil, which is obtained by removing water from the above silicone oil emulsion. Thus, this embodiment of cosmetic raw material is a uniform dispersion of crosslinked silicone particles in a silicone oil. The silicone oil and the crosslinked silicone particles contained in this embodiment of cosmetic raw material are otherwise the same as they are defined above. Thus, this embodiment of cosmetic raw material is adapted and can be used as a nonaqueous cosmetic raw material.

In a further embodiment of the invention, a cosmetic product is composed of a cosmetic raw material which includes the silicone oil emulsion in combination with another cosmetic raw material. A cosmetic product according to this further embodiment of the invention can be in the form of soap, a body shampoo, facial cleanser, or similar cleansing cosmetic, a cosmetic water, cream, milky cream cleanser, pack, or similar basic cosmetic, a face powder, foundation, similar basic makeup, a lipstick, rouge, eyeshadow, eyeliner, mascara, or similar eye makeup, a nail polish or similar manicure related product, a shampoo, hair rinse, hair styling agent, hair growth agent, hair nutrient, hair dye, a perfume, eau de Cologne, or similar aromatic cosmetic; a toothpaste; a substance for use in the bath; a hair removing cream, shaving lotion, antiperspirant, deodorant, sun protecting lotion, or other cosmetic. These cosmetics may be in the form of water-based solutions, oil based solutions, creams, foams, semisolid, solid, powder, or spray.

The other cosmetic raw material component of this further embodiment of the invention may be avocado oil, almond oil, olive oil, cacao oil, sesame oil, wheat germ oil, safflower oil, shea butter, turtle oil, camellia oil, persic oil, castor oil, grape seed oil, macadamia nut oil, mink oil, egg yolk oil, Japan wax, coconut oil, rose hips oil, hydrogenated oil, or similar fats and oils; orange roughy oil, carnauba wax, candelilla wax, whale wax, jojoba oil wax, montan wax, beeswax, lanolin wax, or similar wax; liquid paraffin, Vaseline, paraffin, ceresin, microcrystalline wax, squalane, or similar hydrocarbon; lauric acid, myristic acid, palmitic acid, stearic acid, oleic acid, behenic acid, undecylic acid, hydroxystearic acid, linoleic acid, lanolin fatty acid, synthetic fatty acids, or similar higher aliphatic acid; ethylene alcohol, isopropyl alcohol, lauryl alcohol, cetyl alcohol, cetostearyl alcohol, stearyl alcohol, oleyl alcohol, behenyl alcohol, lanolin alcohol, hydrogenated lanolin alcohol, hexyl decanol, octyl dodecanol, isostearyl alcohol, or similar alcohol; cholesterol, dihydrocholesterol, phytosterol, or similar sterol; ethyl linoleate, isopropyl myristate, lanolin fatty acid isopropyl ester, hexyl laurate, myristyl myristate, cetyl myristate, octyldodecyl myristate, decyl oleate, octyldodecyl oleate, hexyldecyl dimethyl octanate, cetyl isooctanate, cetyl palmitate, glycerine trimyristate, caprylic capric acid triglyceride, cetyl lactate, myristyl lactate, di-isostearyl maleate, or similar fatty acid ester; glycerin, propylene glycol, 1,3-butylene glycol, polyethylene glycol, sodium d,1-pyrrolidone carboxylate, sodium lactate, sorbitol, sodium hyalurate, or similar moisture retaining agent; a higher aliphatic acid soap, a salt of a higher alcohol sulfuric acid ester, a salt of N-acyl glutaminic acid, a surface active agent such as a salt of a phosphoric acid ester, or similar anionic surface active agent, a cationic surface active agent, a betaine, amino acid, imidazoline, lecithin, or similar amphoteric surface active agent, a polyhydric alcohol ester type surface active agent, an ethylene oxide condensation type surface active agent, or a similar nonionic surface active agent; a dye material such as iron oxide or similar colored facial cosmetic, zinc oxide, titanium oxide, zirconium oxide, or similar white facial cosmetic, mica, talc, sericite, or similar dye material; a dimethylpolysiloxane, methylphenylpolysiloxane, octamethylcyclotetrasiloxane, decamethylcylopentasiloxane, a polyether modified silicone oil, an amino modified silicone oil, or similar silicone oil; purified water; carrageenan, alginic acid, an alginic acid salt, acacia gum, tragacanth, pectin, starch, xanthan gum, polyvinyl alcohol, polyvinyl pyrrolidone, sodium polyacrylate, polyethylene glycol, or similar thickener; an ultraviolet absorber, antiseptic, anti-inflammatory agent, an agent for controlling perspiration, an anticorrosion agent, fragrance, antioxidant, pH adjusting agent, a makeup component, or an aerosol propellant.

When the cosmetic is applied to hair, the other cosmetic raw material component of this further embodiment of the invention may be an oil or fat, surface active agent, film forming agent, antidandruff agent, antioxidant, or moisturizer.

Examples of currently used oils and fats are microcrystalline wax, paraffin wax, whale wax, beeswax, Japan wax, sucrose wax, or similar wax; liquid paraffin, alpha-olefin oligomer, squalene, or similar hydrocarbon oil; cetyl alcohol, stearyl alcohol, isostearyl alcohol, hydrogenated castor oil derivative alcohol, behenyl alcohol, lanolin alcohol, or similar higher alcohol; palmitic acid, myristic acid, oleic acid, stearic acid, hydroxy stearic acid, behenic acid, castor fatty acid, coconut fatty acid, or similar higher fatty acid; olive oil, coconut oil, rapeseed oil, palm oil, palm kernal oil, castor oil, hydrogenated castor oil, arachin oil, beef tallow, hydrogenated beef tallow, jojoba oil, hydrogenated jojoba oil; glycerine monostearate, glycerine monooleate, glycerine dipalmitate, glycerine trimyristate, oleyl oleate, stearyl isostearate, palmityl behenate, isopropyl palmitate, stearyl acetate, dihydroxy stearic acid ester, or similar ester; low molecular weight silicone oil having a linear, branched, or cyclic molecular structure, aminomodified silicone oil, fatty acid-modified silicone oil, alcohol-modified silicone oil, polyether-modified silicone oil, phosphoryl-containing silicone oil, sulfur-containing silicone oil, fluoroalkyl-containing silicone oil, alkyl-modified silicone oil, epoxy-modified silicone oil, or similar silicone oil; high molecular weight silicone oil mixed with a liquid or gum at room temperature; or a thermoplastic silicone resin.

Examples of currently used surface active agents are nonionic surface active agents such as glyceryl monostearate, or similar glyceryl fatty acid esters; sorbitan monopalmitate, or similar sorbitan fatty acid esters; polyoxyethylene stearate, polyoxyethylene sorbitan monolaurate, or polyoxyethylene fatty acid esters; polyoxyethylene phenyl ether, polyoxyethylene castor oil, or polyoxyethylene hydrogenated castor oil; cationic surface active agents such as stearyl trimethyl ammonium chloride, behenyl trimethyl ammomium chloride, or monoalkyl trimethyl ammonium salts; distearyl dimethyl ammonium chloride, dibehenyl dimethyl ammonium chloride, or dialkyl dimethyl ammonium salts; and amphoteric surface active agents.

Examples of currently used film forming agents are polymers made with (meta)acryl monomers, or (meta)acryl monomer and silicone, poly(acylalkylenemines), poly(N-methylpyrrolidones), fluoro containing organic or amino modified silicone resins, and nonmodified silicone resins.

Examples of currently used antidandruff agents are sulfur, selenium sulfide, zinc pyrithione, salicylic acid, and 2,4,4'-trichloro-2'-hydroxy-diphenyl ether.

Examples of currently used antioxidants are butylated hydroxyanisole, butylated hydroxytoluene, and gamma-oryzanol.

Examples of currently used moisturizers are 2-methyl-2, 4-pentanediol, polyethylene glycol, sodium pyroglutaminate, propylene glycol, sorbitol, and glycerin.

The other hair cosmetic raw material component of this further embodiment of the invention may be squalane, lanolin, perfluoropolyether cationic polymer, or similar feel additive; ethanol, isopropanol, 1,3-butylene glycol, ethylene glycol, propylene glycol, glycerin, or similar freeze-thaw agent; ethylene diamine tetraacetate, ethan-1-hydroxy-1,1-diphosphonic acid, their salts, or similar chelating agents; 2-hydroxy-4-methoxybenzophenone, or similar benzophenone derivatives; 2-(2'-hydroxy-5'-methylphenyl)-benzotriazole, or similar benzotriazoles; cinnamate, or similar ultraviolet absorbents; fingicides; dipotassium glycyrrhizinate, tocopheryl acetate, or similar anti-inflammatory agent; antiseptics; pigments, dyes, or similar coloring agents, aerosol propellants; vitamins; and fragrances.

When the hair cosmetic product is a water-based cosmetic product, the other hair cosmetic raw material component of this further embodiment of the invention may be purified water; xanthan gum, guar gum, carboxymethylcellulose, polyvinyl alcohol, polyvinylpyrrolidone, carboxyvinylpolymer, hydroxyethyl cellulose, polyoxyethylene glycol distearate, or similar water soluble polymer for a stabilizer or hair setting agent; ethanol; or similar thickener.

Based on components other than moisture, i.e., solids, the amount of these other cosmetic raw materials of this further embodiment of the invention, should be within the range of 0.1 to 99.9 percent by weight, preferably 0.5 to 99 percent by weight, based on the weight of the cosmetic product. This is because the effect of the cosmetic product will be lost if the other cosmetic raw material used with the silicone oil emulsion is present in an amount exceeding the upper limit of the range. On the other hand, it will be difficult to improve its sense of use if the other cosmetic raw material is used with the silicone oil emulsion in an amount below the lower limit of the range.

A further embodiment of the invention, as noted above, is a cosmetic product which is prepared from the silicone composition in combination with another cosmetic raw material. This embodiment is essentially the same as the embodiment just described, except that the components used in this further embodiment are the silicone composition, which is the silicone oil emulsion with its water removed, and one or more of the other cosmetic raw materials listed above. In this additional embodiment, the other cosmetic raw material should be used in an amount of 0.5 to 99.0 percent by weight, preferably 1.0 to 95 percent, based on the weight of the cosmetic product. If the amount of the other cosmetic raw material exceeds the upper limit of this range, the effect of the invention in cosmetic products will be lost. If the amount of the other cosmetic raw material is less than the lower limit of the range, it will be difficult to improve its sense of use.

The fmal embodiment of the invention is a method for preparing cosmetic products by compounding the silicone oil emulsion with another cosmetic raw material. The silicone oil and the crosslinked silicone particles or powder can be uniformly dispersed in the cosmetic product without the use of special equipment and without application of high shear force. Thus, it can be prepared in a cyclic or continuous system, including machines such as homomixers, paddle mixers, Henschel mixers, homodispersers, colloid mixers, propeller type stirrers, homodispersers, homogenizers, in line continuous emulsifiers, ultrasonic emulsifiers, and vacuum kneaders.

Cosmetic products can also be prepared by mixing the silicone oil emulsion all or only part of the other cosmetic raw material, and then removing the water. If necessary, it can be again mix with another cosmetic raw material to prepare a cosmetic product with uniformly dispersed silicone oil and crosslinked silicone particles. Water can be removed using a vacuum treatment, heating, drying in air, or contact with a water absorbing agent.

EXAMPLES

The following examples are set forth to illustrate cosmetic raw materials, cosmetic products, and methods of manufacturing cosmetic products of the invention in more detail.
Practical Examples In the examples, values of viscosity were measured at 25° C. The procedures for determining the average diameter of drops in the silicone oil emulsion, the average diameter of the crosslinked silicone particles, and the characteristics of silicone compositions are described below.
Average Diameter of Drops in the Silicone Oil Emulsion The diameter of drops in the silicone oil emulsion was measured with a Model LA-500 laser diffraction particle distribution measurement instrument made by Horiba Seisakusho Company. The median diameter obtained, i.e., a drop diameter corresponding to 50 percent of the accumulated distribution, was defined as the average drop diameter.
Stability of the Silicone Oil Emulsion 180 ml of silicone oil emulsion were sealed in a 225 ml glass bottle which was 105 mm deep and 50 mm in diameter, and kept for one week in the bottle at room temperature. The thickness of any layer of water which separated from the silicone oil emulsion was then measured.
Dispersibility of Crosslinked Silicone Particles The silicone oil emulsion was dried in air on a glass plate, and then the shape, aggregation, and distribution of the crosslinked silicone particles were observed under a stereoscopic microscope. Structures with a dispersion of primary particles were designated by the symbol "O", aggregated particles with a size of several hundred microns and primary particles exceeding 500 $\mu$m were designated by the symbol "x", and particles having an intermediate dimension between the two were designated by the symbol "Δ".
Average Diameter of Crosslinked Silicone Particles The silicone oil emulsion was dried in air on a glass plate, and then a sample was prepared under a stereoscopic microscope by accumulating the crosslinked silicone particles. The collected sample was observed under an electronic microscope, and an average particle diameter was determined based on 10 of the crosslinked silicone particles.
Viscous Elastic Properties of the Silicone Composition A storage elasticity coefficient G' (in units of $10^3$ dyne/$cm^2$), a loss elasticity coefficient G" (in units of $10^3$ dyne/$cm^2$), and a loss tan δ were measured with an ARES viscosimeter manufactured by Reometric Scientific Company, Incorporated. Measurements were carried out at room temperature using 25 mm parallel plates, a 0.5 to 0.6 mm gap, 10 percent strain, and 0.1 to 50 rad/s oscillation frequency.

Preparation of Cosmetic Raw Material

A cosmetic raw material was prepared as described below.

Reference Example 1

First, a crosslinkable silicone composition was prepared by mixing 18.8 parts by weight of a dimethylpolysiloxane having a viscosity of 400 mPa.s and having dimethylvinylsiloxy groups on both of its molecular terminals, 1.2 parts by weight of a 30 mPa.s viscosity copolymer of methylhydrogen siloxane and dimethylsiloxane having trimethylsiloxy groups on both of its molecular terminals and 0.5 percent by weight content of silicon bonded hydrogen, and 80 parts by weight of a 100 mPa.s viscosity dimethylpolysiloxane having trimethylsiloxy groups on both of its molecular terminals. This crosslinkable silicone composition was then combined with 53 parts by weight of a 3 percent by weight aqueous solution of polyoxyethylene nonyl phenyl ether having an HLB of 13.1. After being emulsified, 50 parts by weight of pure water were added to the mixture. The result was an aqueous emulsion of a crosslinkable silicone composition.

A separately prepared aqueous emulsion of a platinum catalyst containing a complex of platinum and 1,1 -divinyl-1,1,3,3-tetramethoxydisiloxane as the main component was added to the aqueous emulsion of crosslinkable silicone composition prepared immediately above. The components were uniformly mixed so that the content of metalic platinum in weight units was equal to about 20 ppm. The average diameter of platinum catalyst particles was equal to 0.05 $\mu$m, and the concentration of metallic platinum was 0.05 percent by weight. Again, the result was an aqueous emulsion of a crosslinkable silicone composition.

This emulsion was kept intact at room temperature for one day, and then it was subjected to hydrosilation, whereby a silicone oil emulsion was obtained containing crosslinked. silicone particles present in the drops of silicone oil, which were in turn dispersed in water. This product was designated Cosmetic Raw Material (A).

It was transferred to a 5 cm diameter aluminum plate, and water was removed from the emulsion by drying it in air while maintaining it in an air draft for 3 days. The result was a silicone composition consisting of the silicone oil and the silicone particles having a cream like form. Observation of the silicone composition under a stereoscopic microscope showed that it consisted of spherically shaped crosslinked silicone particles dispersed in the silicone oil.

Reference Example 2

An aqueous emulsion of a crosslinked silicone composition was prepared following the method in Reference Example 1 except that 80 parts by weight of a 6 mPa.s viscosity dimethylpolysiloxane having trimethylsiloxy groups on both of its molecular terminals was used instead of 80 parts by weight of an 100 mPa.s viscosity dimethypolysiloxane having trimethylsiloxy groups on both of its molecular terminals. The emulsion was subjected to hydrosilation and a silicone oil emulsion was obtained having crosslinked silicone particles contained in the silicone oil drops, which were in turn dispersed in water.

The silicone composition consisting of silicone oil and crosslinked silicone particles was prepared by removing water from the emulsion as described in Reference Example 1. The obtained composition had a cream like appearance and was designated as COSMETIC RAW MATERIAL (B). Observation of the composition under a stereoscopic microscope showed that it consisted of spherically shaped crosslinked silicone particles uniformly dispersed in the silicone oil.

Reference Example 3

A mixture (I) was prepared by uniformly mixing 100 parts by weight of a dimethylpolysiloxane having a viscosity of 1,000 mPa.s, hydroxyl groups on both of its molecular terminals, and a content of hydroxyl groups of 1.3 percent by weight; 10 parts by weight of a 10 mPa.s viscosity methylhydrogen polysiloxane having trimethylsiloxy groups on both of its molecular terminals and containing 1.5 percent by weight of silicon bonded hydrogen; and 50 parts by weight of a 1000 mPa.s viscosity dimethylpolysiloxane having trimethylsiloxy groups on both of its molecular terminals.

A mixture (II) was prepared by uniformly mixing 100 parts by weight of a dimethylpolysiloxane having a viscosity of 1,000 mPa.s, hydroxyl groups on both of its molecular terminals, and a content of hydroxyl groups of 1.3 percent by weight; 50 parts by weight of a 1000 mPa.s viscosity dimethylpolysiloxane having trimethylsiloxy groups on both of its molecular terminals; and 1.5 parts by weight of dibutyltin dioctoate.

After uniformly mixing mixtures (I) and (II) in a 1:1 weight ratio, the composition was combined with a mixture of 5 parts by weight of Tergitol TMN-6, a product of the Union Carbide Company and an ethylene oxide adduct of trimethylnonanol, and 1700 parts by weight of ion exchanged water. This product was then emulsified. The resulting emulsion was sprayed in a spray drier having an input temperature of 300° C. and an output temperature of 100° C. After removal of the water, crosslinked silicone particles were obtained with a yield of about 98 percent. This product was designated as Cosmetic Raw Material (C). The crosslinked silicone particles had rubber like properties and were spherical in shape. No bleeding of the silicone oil from the crosslinked silicone particles was observed.

Reference Example 4

In a planetary mixer, a mixture was prepared by combining 44.5 parts by weight of a dimethylpolysiloxane having a viscosity of 5 mPa.s and vinyldimethylsiloxy groups on both of its molecular terminals; 100 parts by weight of a 20 mPa.s viscosity methylhydrogen polysiloxane with 1.5 percent by weight silicon bonded hydrogen atoms, and trimethylsiloxy groups on both of its molecular terminals; and 758 parts by weight of a 6 mPa.s viscosity dinethylpolysiloxane having trimethylsiloxy groups on both of its molecular terminals. A crosslinkable silicone composition was then prepared by adding 0.5 parts by weight of a 2 percent by weight isopropanol solution of chloroplatinic acid. This crosslinkable silicone composition was heated to 70–80° C. and stirred for 2 hours to perform the hydrosilation and crosslinking of the composition. This composition was kneaded between three rollers under shear conditions and a paste like silicone composition was prepared. This paste like composition was designated as Cosmetic Raw Material (D). Observation under a general purpose microscope showed that the silicone particles were dispersed in the silicone oil and had an irregular shape, that the dispersion was not uniform, and that the diameter of the crosslinked silicone particles was in the range of 100 to 500 μm.

TABLE 1

| Example Type<br>Item | Ref. Ex. 1<br>A | Ref. Ex. 2<br>B | Ref. Ex. 3<br>C | Ref Ex. 4<br>D |
|---|---|---|---|---|
| Average Particle Diameter, μm in Silicone Oil Emulsion | 8 | 7 | 5 | — |
| Stability (mm) | 0 | 0 | 49 | — |
| Dispersibility of Crosslinked Silicone Particles | ○ | ○ | X | — |
| Average Particle Diameter, μm | 3 | 3 | 5 | 17 |
| G' of Silicone Composition | | | | |
| 1 rad/s | 9.7 | 15 | — | 5.0 |
| 10 rad/s | 13 | 37 | — | 7.5 |
| G" of Silicone Composition | | | | |
| 1 rad/s | 6.3 | 16 | — | 4.7 |
| 10 rad/s | 11 | 21 | — | 4.0 |

Because of the nature of the crosslinked silicone particles in Reference Example 4 some measurements were not carried out.

Cosmetic Products and Methods for Manufacture

The following examples show some of the cosmetic products of this invention. Some characteristics which were evaluated for these products and procedures used in the evaluations are also set forth below.

Sensation of Touch of Cosmetic Products with the Fingers

Each member of a panel of 10 people touched a cosmetic product with their fingers. The symbol ○ was used to designate that 8 to 10 panel members felt that the cosmetic product was pleasant to the touch, the symbol Δ was used to designate that 4 to 7 panel members felt that the cosmetic product was pleasant to the touch, and the symbol X was used to designate that less than 3 panel members felt that the cosmetic product was pleasant to the touch.

Sensation of Touch of Cosmetic Products with the Skin

Each member of a panel of 10 people participated in this phase of the tests. The symbol ○ was used to designate that 8 to 10 panel members felt that the cosmetic product was pleasant to touch with their skin, the symbol Δ was used to designate that 4 to 7 panel members felt that the cosmetic product was pleasant to touch with their skin, and symbol X was used to designate that less than 3 panel members felt that the cosmetic product was pleasant to touch with their skin.

Dispersity of Crosslinked Particles in Cosmetic Products

The cosmetic product was applied to a glass plate in the form of a thin layer and then the diameter of the crosslinked silicone particles in the cosmetic product were measured under an optical microscope. The dispersity of the crosslinked silicone particles in the cosmetic product was evaluated on the basis of the percentage of the particles having a diameter less than 10 μm, the percentage of the particles having a diameter between 10 and 50 μm, and the percentage of the particles having a diameter exceeding 50 μm.

Practical Example 1

A mixture was prepared from 52 parts by weight of Cosmetic Raw Material (A), 5 parts by weight of octyl p-methoxy cinnamate, 1 part by weight of the α-monoisostearyl glyceryl ether of polyoxyethylene sorbitan mono-oleic acid ester, 2 parts by weight of beeswax, 2 parts by weight of anhydrous lanolin, 10 parts by weight of squalane, 10 parts by weight of liquid paraffin, 19 parts by weight of purified water, and an appropriate amount of an antiseptic agent and perfume. The mixture was stirred in a homodisperser for 3 hours at 2500 rpm (262 rad/s) and an emulsified cosmetic product was formed. Results of the evaluation of this product are shown in Table 2.

Practical Example 2

A mixture was prepared from 52 parts by weight of Cosmetic Raw Material (B), 5 parts by weight of octyl p-methoxy cinnamate, 1 part by weight of the α-monoisostearyl glyceryl ether of polyoxyethylene sorbitan mono-oleic acid ester, 2 parts by weight of beeswax, 2 parts by weight of anhydrous lanolin, 10 parts by weight of squalane, 10 parts by weight of liquid paraffin, 19 parts by weight of purified water, and an appropriate amount of an antiseptic agent and perfume. The mixture was stirred in a homodisperser for 3 hours at 2500 rpm (262 rad/s) and an emulsified cosmetic product was formed. Results of the evaluation of the product are shown in Table 2.

Comparative Example 1

A mixture was prepared from 3 parts by weight of Cosmetic Raw Material (C), 24 parts by weight of an emulsion with a 50 percent concentration of a 100 mPa.s viscosity dimethylpolysiloxane capped with trimethylsiloxy groups on both of its molecular terminals and having quadruple the amount of crosslinked silicone particles, 5 parts by weight of octyl p-methoxy cinnamate, 1 part by weight of the α-monoisostearyl glyceryl ether of polyoxyethylene sorbitan mono-oleic acid ester, 2 parts by weight of beeswax, 2 parts by weight of anhydrous lanolin, 10 parts by weight of squalane, 10 parts by weight of liquid paraffin, 54 parts by weight of purified water, and an appropriate amount of an antiseptic agent and perfume. The mixture was stirred in a homodisperser for 3 hours at 2500 rpm (262 rad/s) and an emulsified cosmetic product was formed. Results of the evaluation of the product are shown in Table 2.

TABLE 2

| Example Item | Pr. Ex. 1 | Pr. Ex 2 | Comp. Ex. 1 |
|---|---|---|---|
| Feeling of touch by the fingers | ◯ | ◯ | Δ(rough) |
| Feeling of touch by the skin | ◯ | ◯ | Δ(rough) |
| Dispersity of crosslinked silicone particles in the cosmetic product (particle diameter) | | | |
| ≦10 μm | 100% | 100% | 0% |
| 10 μm <, ≦50 μm | 0% | 0% | 70% |
| 50 μm ≦ | 0% | 0% | 30% |

Practical Example 3

A mixture was prepared from 40 parts by weight of Cosmetic Raw Material (B), 1 part by weight of a silicone treated titanium oxide, 5 parts by weight of octyl p-methoxy cinnamate, 10 parts by weight of a 20 mPa.s viscosity dimethylpolysiloxane capped with trimethylsiloxy groups on both of its molecular terminals, 3 parts by weight of a polyoxyethylene 40 mole adduct hydrogenated castor oil, 30 parts by weight of squalane, 5 parts by weight of glycerine, 3 parts by weight of beeswax, and an appropriate quantity of an antiseptic agent, perfume, and purified water. The mixture was stirred in a Henschel mixer for 5 minutes at 1500 rpm (157 rad/s) and a cream like cosmetic product was formed. Results of the evaluation of the product are shown in Table 3.

Comparative Example 2

A mixture was prepared from 20 parts by weight of Cosmetic Raw Material (D), 1 part by weight of a silicone treated titanium oxide, 5 parts by weight of octyl p-methoxy cinnamate, 10 parts by weight of a 20 mPa.s viscosity dimethylpolysiloxane capped with trimethylsiloxy groups on both of its molecular terminals, 3 parts by weight of a polyoxyethylene 40 mole adduct hydrogenated castor oil, 30 parts by weight of squalane, 5 parts by weight of glycerine, 3 parts by weight of beeswax, and an appropriate quantity of antiseptic agent, perfume, and purified water. The mixture was stirred in a Henschel mixer for 5 minutes at 1500 rpm (157 rad/s) and a cream like cosmetic product was formed. Results of the evaluation of the product are shown in Table 3.

TABLE 3

| Example Item | Pr. Ex. 3 | Comp. Ex. 2 |
|---|---|---|
| Feeling of touch by the fingers | ◯ | ◯ |
| Feeling of touch by the skin | ◯ | Δ(rough) |
| Dispersity of crosslinked silicone particles in the cosmetic product (particle diameter) | | |
| ≦10 μm | 100% | 0% |
| 10 μm <, ≦50 μm | 0% | 60% |
| 50 μm ≦ | 0% | 40% |

Practical Example 4

A mixture was prepared from 14 parts by weight of Cosmetic Raw Material (B), 2 parts by weight of 1,3-butylene glycol, 50 parts by weight of ethanol, 1 part by weight of a polyether modified silicone oil which was a product of Dow Corning Toray Silicone Co., Ltd. identified as their material SH 3771, 4 parts by weight of propylene glycol, 1 part by weight of polyoxyethylene 15 mole adduct nonyl ether, 1 part by weight of a silicone treated titanium oxide, and appropriate quantities of an antiseptic agent, perfume, and purified water. The mixture was stirred in a Henschel mixer for 5 minutes at 1500 rpm (157 rad/s). Results of the evaluation of the product are shown in Table 4.

Comparative Example 3

A mixture was prepared from 1 part by weight of Cosmetic Raw Material (C), 2 parts by weight of an emulsion having a 50 percent concentration of a 100 mPa.s viscosity dimethylpolysiloxane capped with trimethylsiloxy groups on both of its molecular terminals, 4 parts by weight of purified water, 2 parts by weight of 1,3-butylene glycol, 50 parts by weight of ethanol, 1 part by weight of the Dow Corning Toray Silicone Co., Ltd. SH 3771 polyether modified silicone oil, 4 parts by weight of propylene glycol, 1 part by weight of polyoxyethylene 15 mole adduct oleyl ether, 1 part by weight of a silicone treated titanium oxide, and an appropriate quantity of antiseptic agent, perfume, and purified water. The mixture was stirred in a Henschel mixer for 5 minutes at 1500 rpm (157 rad/s). Results of the evaluation of the product are shown in Table 4.

TABLE 4

| Example Item | Pr. Ex. 4 | Comp. Ex. 3 |
|---|---|---|
| Feeling of touch by the fingers | ○ | Δ(rough) |
| Feeling of touch by the skin | ○ | Δ(rough) |
| Dispersity of crosslinked silicone particles in the cosmetic product (particle diameter) | | |
| ≦10 μm | 100% | 0% |
| 10 μm <,≦50 μm | 0% | 70% |
| 50 μm≦ | 0% | 30% |

Practical Example 5

The Cosmetic Raw Material (A) prepared in Reference Example 1 was spread over a metal plate in the form of a 5 mm thick layer and dried in air for 1 week at room temperature. The result was a paste like silicone composition having crosslinked silicone particles uniformly dispersed in a silicone oil. This silicone composition was designated Cosmetic Raw Material (A'). The decrease in weight of Cosmetic Raw Material (A') after heating it for 30 minutes at 105° C. was 0.2 percent by weight.

A mixture was prepared in a Henschel mixer by mixing 10 parts by weight of Cosmetic Raw Material (A'), 10 parts by weight of decamethylcyclopentasiloxane, 10 parts by weight of silicone treated titanium dioxide, and an appropriate quantity of perfume. A rouge was prepared using this mixture by adding and mixing 5 parts by weight of a silicone treated zinc white, 55 parts by weight of a silicone treated talc and silicone treated pigment, and an appropriate amount of a perfume. The properties of the rouge are shown in Table 5.

Comparative Example 4

A rouge was prepared as in Practical Example 5 except that Cosmetic Raw Material (D) was used instead of Cosmetic Raw Material (A'). The properties of this rouge are shown in Table 5.

TABLE 5

| Example Item | Pr. Ex. 5 | Comp. Ex. 4 |
|---|---|---|
| Feeling of touch by the fingers | ○ | Δ(rough) |
| Feeling of touch by the skin | ○ | Δ(rough) |
| Dispersity of crosslinked silicone particles in the cosmetic product (particle diameter) | | |
| ≦10 μm | 100% | 0% |
| 10 μm <,≦50μm | 0% | 70% |
| 50 μm≦ | 0% | 30% |

Practical Example 6

A planetary mixer was used to mix 100 parts by weight of Cosmetic Raw Material (B) with 10 parts by weight of a silicone rubber powder having 4 μm average diameter particles sold under the trade name TOREFIL E-506C by Dow Corning Toray Silicone Co., Ltd. Water was then removed from this mixture using a vacuum at 50° C., and a uniform paste like silicone composition was prepared. The heating loss of this paste like silicone composition was less than about 0.3 percent by weight after it had been heated for 30 minutes at 105° C. A foundation was then prepared by mixing 40 parts by weight of the paste like silicone composition in a Henschel mixer along with 10 parts by weight of sericite, 10 parts by weight of a silicone treated titanium dioxide, 1.5 parts by weight of a silicone treated iron oxide red, 4 parts by weight of a silicone treated iron oxide yellow, 0.3 parts by weight of a silicone treated iron oxide black, 4 parts by weight of the ARISTO® wax product of Union Oil Company of California, 1.3 parts by weight of carnauba wax, 33 parts by weight of squalane, 1 part by weight of sorbitan sesquistearate, 3 parts by weight of kaolin, and an appropriate quantity of perfume. Properties of the foundation are shown in Table 6.

Comparative Example 5

A foundation was prepared using the method in Practical Example 6 except that Cosmetic Raw Material (D) was used instead of the paste like silicone composition. The properties of the foundation so obtained are shown in Table 6.

TABLE 6

| Example Item | Pr. Ex. 6 | Comp. Ex. 5 |
|---|---|---|
| Feeling of touch by the fingers | ○ | Δ(rough) |
| Feeling of touch by the skin | ○ | Δ(rough) |
| Dispersity of crosslinked silicone particles in the cosmetic product (particle diameter) | | |
| ≦10 μm | 100% | 0% |
| 10 μm <,≦50 μm | 0% | 70% |
| 50 μm≦ | 0% | 30% |

The data relating to the dispersity of the crosslinked silicone particles used in Comparative Example 5 includes the TOREFIL E-506C silicone rubber powder of Dow Corning Toray Silicone Co., Ltd., as the other cosmetic raw material.

Preparation of Hair Cosmetic Raw Material

A hair cosmetic raw material was prepared as described below.

Reference Example 5

First, a crosslinkable silicone composition was prepared by mixing 15.7 parts by weight of a dimethylpolysiloxane having a viscosity of 400 mPa.s and having dimethylvinylsiloxy groups on both of its molecular terminals; 1.0 parts by weight of a 30 mPa.s viscosity copolymer of methylhydrogen siloxane and dimethylsiloxane having trimethylsiloxy groups on both of its molecular terminals and 0.5 percent by weight content of silicon bonded hydrogen, and 83.3 parts by weight of a 20 mPa.s viscosity dimethylpolysiloxane having trimethylsiloxy groups on both of its molecular terminals. This crosslinkable silicone composition was then combined with 53 parts by weight of a 3 percent by weight aqueous solution of polyoxyethylene nonyl phenyl ether having an HLB of 13.1. After being emulsified, 50 parts by weight of pure water were added to the mixture. The result was an aqueous emulsion of a crosslinkable silicone composition.

A separately prepared aqueous emulsion of a platinum catalyst containing a complex of platinum and 1,3-divinyl-1,1,3,3-tetramethoxydisiloxane as the main component was added to the aqueous emulsion of crosslinkable silicone composition prepared immediately above. The components were uniformly mixed so that the content of metallic platinum in weight units was equal to about 20 ppm. The average diameter of platinum catalyst particles was equal to 0.05 $\mu$m, and the concentration of metallic platinum was 0.05 percent by weight. Again, the result was an aqueous emulsion of a crosslinkable silicone composition.

This emulsion was kept intact at room temperature for one day, and then it was subjected to hydrosilation, whereby a silicone oil emulsion was obtained containing crosslinked silicone particles present in the drops of silicone oil, which were in turn dispersed in water. This product was designated Hair Cosmetic Raw Material (E).

It was transferred to a 5 cm diameter aluminum plate, and water was removed from the emulsion by drying it in air while maintaining it in an air drafi for 3 days. The result was a silicone composition consisting of the silicone oil and the silicone particles having a cream-like form. Observation of the silicone composition under a stereoscopic microscope showed that it consisted of spherically shaped crosslinked silicone particles dispersed in the silicone oil.

Reference Example 6

An aqueous emulsion of a crosslinked silicone composition was prepared following the method in Reference Example 5 except that 83.3 parts by weight of a 300 mPa.s viscosity mixture consisting of 80 parts by weight of decamethylpentasiloxane and 3.3 parts by weight of a 20,000,000 mPa.s viscosity dimethylpolysiloxne having trimethylsiloxy groups on both of its molecular terminals was used instead of 83.3 parts by weight of a 20 mPa.s viscosity dimethpolysiloxane having trimethylsiloxy groups on both of its molecular terminals. The emulsion was subjected to hydrosilation and a silicone oil emulsion was obtained having crosslinked silicone particles contained in the silicone oil drops, which were in turn dispersed in water.

The silicone composition consisting of silicone oil and crosslinked silicone particles was prepared by removing water from the emulsion as described in Reference Example 5. The obtained composition had a cream-like appearance and was designated as Hair Cosmetic Raw Material (F). Observation of the composition under a stereoscopic microscope showed that it consisted of spherically shaped crosslinked silicone particles uniformly dispersed in the silicone oil.

Reference Example 7

First, a crosslinkable silicone composition was prepared by mixing 15.0 parts by weight of a copolymer of dimethylsiloxane and methylvinylsiloxane having a viscosity of 400 mPa.s and having dimethylvinylsiloxy groups on both of its molecular terminals, 1.7 parts by weight of a 50 mPa.s viscosity copolymer of methylhydrogen siloxane and dimethylsiloxane having trimethylsiloxy groups on both of its molecular terminals and 0.44 percent by weight content of silicon bonded hydrogen, and 83.3 parts by weight of a 20 mPa.s viscosity dimethylpolysiloxane having trimethylsiloxy groups on both of its molecular terminals. This crosslinkable silicone composition was then combined with 53 parts by weight of a 3 percent by weight aqueous solution of polyoxyethylene nonyl phenyl ether having an HLB of 13.1. After being emulsified, 50 parts by weight of pure water were added to the mixture. The result was an aqueous emulsion of a crosslinkable silicone composition.

A separately prepared aqueous emulsion of a platinum catalyst containing a complex of platinum and 1,3-divinyl-1,1,3,3-tetramethoxydisiloxane as the main component was added to the aqueous emulsion of crosslinkable silicone composition prepared immediately above. The components were uniformly mixed so that the content of metallic platinum in weight units was. equal to about 20 ppm. The average diameter of platinum catalyst particles was equal to 0.05 $\mu$m, and the concentration of metallic platinum was 0.05 percent by weight. Again, the result was an aqueous emulsion of a crosslinkable silicone composition.

This emulsion was kept intact at room temperature for one day, and then it was subjected to hydrosilation, whereby a silicone oil emulsion was obtained containing crosslinked silicone particles present in the drops of silicone oil, which were in turn dispersed in water. This product was designated Hair Cosmetic Raw Material (G).

It was transferred to a 5 cm diameter aluminum plate, and water was removed from the emulsion by drying it in air while maintaining it in an air draft for 3 days. The result was a silicone composition consisting of the silicone oil and the silicone particles having a cream-like form. Observation of the silicone composition under a stereoscopic microscope showed that it consisted of spherically shaped crosslinked silicone particles dispersed in the silicone oil.

Reference Example 8

First, a crosslinkable silicone composition was prepared by mixing 94.0 parts by weight of a dimethylpolysiloxane having a viscosity of 400 mPa.s and having dimethylvinylsiloxy groups on both of its molecular terminals, and 60 parts by weight of a 30 mPa.s viscosity copolymer of methylhydrogen siloxane and dimethylsiloxane having trimethylsiloxy groups on both of its molecular terminals and 0.5 percent by weight content of silicon bonded hydrogen. This crosslinkable silicone composition was then combined with 53 parts by weight of a 3 percent by weight aqueous solution of polyoxyethylene nonyl phenyl ether having an HLB of 13.1. After being emulsified, 50 parts by weight of pure water were added to the mixture. The result was an aqueous emulsion of a crosslinkable silicone composition.

A separately prepared aqueous emulsion of a platinum catalyst containing a complex of platinum and 1,3-divinyl-1,1,3,3-tetramethoxydisiloxane as the main component was added to the aqueous emulsion of crosslinkable silicone composition prepared immediately above. The components were uniformly mixed so that the content of metallic platinum in weight units was equal to about 20 ppm. The average diameter of platinum catalyst particles was equal to 0.05 μm, and the concentration of metallic platinum was 0.05 percent by weight. Again, the result was an aqueous emulsion of crosslinkable silicone composition.

This emulsion was kept intact at room temperature for one day, and then it was subjected to hydrosilation, whereby a silicone oil emulsion was obtained containing crosslinked

Reference Example 10

A mixture was prepared by uniformly mixing 360 parts by weight of a dimethylpolysiloxane having a viscosity of 1,000,000 mPa.s, and trimethylsiloxy groups on both of its molecular terminals; and 240 parts by weight of a dimethylpolysiloxane having a viscosity of 20 mpa.s, and trimethylsiloxy groups on both of its molecular terminals. This mixture was then combined with 15 parts by weight of polyoxyethylene lauryl ether having an HLB of 10.5, 35 parts by weight of polyoxyethylene lauryl ether having an HLB of 16.7, and 40 parts by weight of pure water. After being emulsified, 310 parts by weight of pure water were added to the mixture. The result was an aqueous emulsion of a silicone oil. The emulsion was designated as Hair Cosmetic Raw Material (J).

TABLE 7

| Example | Ref. Ex. 5 | Ref. Ex. 6 | Ref. Ex. 7 | Ref. Ex. 8 | Ref. Ex. 9 | Ref. Ex. 10 |
|---|---|---|---|---|---|---|
| Type Item | E | F | G | H | I | J |
| Avg. Particle Diameter, μm in Silicone Oil Emulsion | 7 | 7 | 8 | 5 | — | 0.5 |
| Dispersibility of Crosslinked Silicone Particles | ○ | ○ | ○ | X | — | — |
| Average Particle Diameter, μm | 3 | 4 | 3 | 5 | 100–500 | — | silicone particles present in the drops of silicone oil, which were in turn dispersed in water. This product was designated Hair Cosmetic Raw Material (H).

It was transferred to a 5 cm diameter aluminum plate, and water was removed from the emulsion by drying it in air while maintaining it in an air draft for 3 days. The result was silicone particles. The silicone particles were extracted with toluene. The content of the non-crosslinkable silicone oil in the silicone particles was 5 percent by weight.

Reference Example 9

In a planetary mixer, a mixture was prepared by combining 44.5 parts by weight of a dimethylpolysiloxane having a viscosity of 5 mPa.s and vinyldimethylsiloxy groups on both of its molecular terminals; 100 parts by weight of a 20 mPa.s viscosity methylhydrogen polysiloxane with 1.5 percent by weight silicon bonded hydrogen atoms, and trimethylsiloxy groups on both of its molecular terminals; and 758 parts by weight of a 6 mPa.s viscosity dimethylpolysiloxane having trimethylsiloxy groups on both of its molecular terminals. A crosslinkable silicone composition was then prepared by adding 0.5 parts by weight of a 2 percent by weight isopropanol solution of chloroplatinic acid. This crosslinkable silicone composition was heated to 70–80° C. and stirred for 2 hours to perform the hydrosilation and crosslinking of the composition. This composition was kneaded between three rollers under shear conditions and a paste-like silicone composition was prepared. This paste-like composition was designated as Hair Cosmetic Raw Material (I). Observation under a general purpose microscope showed that the silicone particles were dispersed in the silicone oil and had an irregular shape, that the dispersion was not uniform, and that the diameter of the crosslinked silicone particles was in the range of 100 to 500 μm.

Practical Example 7 Through 9 Comparative Examples 6 and 7

The shampoos described below were mixed in the proportions (parts by weight) shown in Table 8. The hair tresses were shampooed with these shampoos. Then, sensations of touch of the hair and improvement rates of combing were evaluated as follows.

Sensation of Touch of the Hair with the Fingers 10 g of 20 cm hair tresses were shampooed with 2.5 percent by weight sodium polyoxyethylene lauryl ether sulfate aqueous solution, and rinsed with heated water. The tresses were dried for 12 hours at 25 degrees centigrade.

The tresses were first dipped in water for 30 seconds and allowed to drip. Then the tresses were shampooed with 1 g of the above shampoos for 1 minute, and rinsed two times with heated water for 20 seconds. The sensation of touch of the dripped tresses and dried tresses which were dried for 12 hours at 25 degrees centigrade, were evaluated.

Improvement in the Rate of Combing 10 g of 20cm hair tresses were shampooed with a 2.5 percent by weight sodium polyoxyethylene ether sulfate aqueous solution and rinsed with heated water. The tresses were dried for 12 hours at 25 degrees centigrade.

The tresses were first dipped in water for 30 seconds and dried by towel for 5 seconds. The tresses were brushed smooth. The combing force of the native hair at 200 mm/min. speed was measured using a tensile testing apparatus. Then the tresses were shampooed with 1 g of the above shampoos, rinsed two times with heated water for 20 seconds, and dried by towel. The combing force of the shampooed hairs at 200 mm/min. speed was measured using a tensile testing apparatus. The improvement in the rates of combing were calculated by the equation: Improvement in rate of combing (%)=100×(A−B)/A, where A is the combing force for native hair, and B is the combing force for shampooed hair

Comparative Example 8

The shampoo was prepared as in Practical Example 5 except that Hair Cosmetic Raw Material (I) was used instead of Hair Cosmetic Raw Material (E). However, the shampoo was not uniform because of the presence of a 100–200 micrometer aggregate of crosslinked silicone particles.

TABLE 8

|  | Pr. Ex. 7 | Pr. Ex. 8 | Pr. Ex. 9 | Comp. Ex. 6 | Comp. Ex. 7 |
|---|---|---|---|---|---|
| Hair Cosmetic Raw Material Composition (parts by weight) | E | F | G | H | J |
| Sodium POE (2 mol adduct) lauryl ether sulfate | 12.0 | 12.0 | 12.0 | 12.0 | 12.0 |
| Hair Cosmetic Raw Material | 5.0 | 5.0 | 5.0 | 5.0 | 5.0 |
| Water | 83.0 | 83.0 | 83.0 | 83.0 | 83.0 |
| Sensation of Touch of the Hair |  |  |  |  |  |
| Dripped Hair | smooth non-creaky | smooth non-creaky | smooth non-creaky | smooth heavy | smooth a little creaky |
| Dried Hair | very smooth good wettability non-creaky | very smooth good wettability non-creaky | very smooth good wettability non-creaky | heavy | smooth very creaky |
| Improvement in Rate of Combing (%) | 35 | 38 | 41 | 7 | 25 |

Practical Example 10 and Comparative Examples 9 and 10

The rinses were prepared by mixing 2 percent by weight of Hair Cosmetic Raw Material (E) or (H), and 98 percent by weight of purified water. Sensation of touch of the hair, the number of crosslinked silicone particle on the hair, and the rinse of 100 percent by weight of purified water were evaluated.

Sensation of Touch of the Hair with the Fingers 10 g of 20cm hair tresses were shampooed with a 2.5 percent by weight sodium polyoxyethylene lauryl ether sulfate aqueous solution and rinsed with heated water. The tresses were dried for 12 hours at 25 degrees centigrade. The tresses were first dipped in the above rinses and dried for 12 hours at 25 degrees centigrade. Sensation of touch of the hair was evaluated as follows.

◯: very good
o: good
Δ: no choice
X: bad

Number of Crosslinked Silicone Particles on a Hair

Rinsed hair was observed by an electron microscope. The number of crosslinked silicone particles on a 100 micrometer hair on one side were counted.

TABLE 9

|  | Pr. Ex. 10 | Comp. Ex. 9 | Comp. Ex. 10 |
|---|---|---|---|
| Hair Cosmetic Raw Material | E | H | none |
| Feeling of touch by the fingers |  |  |  |
| Slipperiness | ◯ | Δ | X |
| Smoothness | ◯ | Δ | X |
| Number of crosslinked silicone particles on hair | 7 | 1 | 0 |

As previously pointed out, the cosmetic raw material of this invention includes a silicone oil and crosslinked silicone particles which can be uniformly dispersed in various cosmetic products. Since these cosmetic products have the cosmetic raw material of the invention combined with other cosmetic raw materials, it has now become possible to provide more uniform dispersions of silicone oils and crosslinked silicone particles in cosmetic products. The resulting cosmetic products in turn have a pleasant sensation when touched by the fingers and the skin, and in addition, they exhibit improved rubbing properties and sensation when they are being used. Methods for manufacturing these cosmetic products allow an efficient production of the cosmetic products.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of treating hair or skin comprising applying to hair or skin a silicone oil in water emulsion consisting essentially of crosslinked silicone particles having an average diameter of about 0.05–100 μm, the crosslinked silicone particles being contained in drops of a silicone oil having an average diameter of about 0.1–500 μm, the drops of the silicone oil containing the crosslinked silicone particles being dispersed in water to form the silicone oil in water emulsion, with the diameter of the crosslinked silicone particles being less than the diameter of the drops of the silicone oil, the silicone oil in water emulsion being produced by dispersing in water a crosslinkable silicone composition that contains a non-crosslinkable silicone oil, a surface active agent, and a catalyst, and conducting a crosslinking reaction.

2. The method according to claim 1 wherein the silicone oil has a viscosity of 1–100,000,000 mPa.s at 25° C.

3. The method according to claim 2 wherein the crosslinked silicone particles are products of a hydrosilation crosslinking reaction or a condensation crosslinking reaction.

* * * * *